United States Patent [19]

Simoons

[11] 4,154,820

[45] May 15, 1979

[54] COMPOSITIONS CONTAINING ALKALI METAL SULFATE SALTS OF CONJUGATED ESTROGENS AND ANTIOXIDANTS AS STABILIZERS

[75] Inventor: Johan R. A. Simoons, Summit, N.J.

[73] Assignee: Akzona Incorporated, Asheville, N.C.

[21] Appl. No.: 836,679

[22] Filed: Sep. 26, 1977

Related U.S. Application Data

[63] Continuation-in-part of Ser. No. 660,304, Feb. 23, 1976, abandoned.

[51] Int. Cl.² ............... A61K 31/00; A61K 31/56; A61K/31/58; A61K/47/00
[52] U.S. Cl. .................. 424/175; 260/397.5; 424/99; 424/100; 424/105; 424/238; 424/239; 424/240; 424/241; 424/242; 424/243;
[58] Field of Search ............ 424/99, 100, 105, 175, 424/182, 238–243; 260/397.5

[56] References Cited

U.S. PATENT DOCUMENTS

| 2,324,348 | 7/1943 | Anderson | 252/367 |
|---|---|---|---|
| 2,834,712 | 5/1958 | Beall | 424/100 |
| 3,644,618 | 2/1972 | Holden | 424/100 |
| 3,666,865 | 5/1972 | Ludwig | 424/346 |
| 3,674,869 | 7/1972 | Ludwig | 424/175 |

OTHER PUBLICATIONS

Modern Drug Ency. & Therap. Index, 9th Ed., 1963, pp. 280–281, 517–521, 1112–1114, 1376, 1389–1390, 1441.
Smith, Chem. Abs., vol. 41, 1947, p. 7484e.
Nazir, Chem. Abs., vol. 56, 1962, p. 2743i–2744a.
Kaufman, Chem. Abs., vol. 58, 1963, pp. 12785h–12786a.
Strenkovskaya, Chem. Abs., vol. 73, 1970, Ab. No. 18447t.
Schroeter, J. Pharm. Sci., vol. 50, Nov. 1961, pp. 891–900.
Smith, J. of Endocrin., vol. 5, 1947, pp. 152–157.
Merck Index, Merck & Co., Rahway, N.J., 7th Ed., 1960, p. 537.

*Primary Examiner*—Anna P. Fagelson
*Attorney, Agent, or Firm*—Robert H. Falk; Charles A. Wendel; Francis W. Young

[57] ABSTRACT

A new and remarkably stable synthesized conjugated estrogen composition comprising one or more selected alkali metal synthetic conjugated estrogen sulfate salts and an effective amount of one or more suitable antioxidants has been found for use in novel and stable therapeutic preparations of a pH of not less than about 7 which are adapted to relieve, inter alia, complaints occurring in the menopausal syndrome and other female complaints. Preferably, the steroids are selected from the sodium and potassium salts of the group consisting of estrone, equilin, 17α-dihydroequilin, and mixtures or conjugates thereof. Most preferably, the preparations are so formulated so that sodium estrone sulfate, sodium equilin sulphate, and 17α-dihydroequilin sodium sulphate as conjugated estrogens are present in a weight ratio of about 6:3:1, respectively and administered in tablets containing 0.625 mg, 1.25 mg, or 2.5 mg of total conjugated estrogens.

10 Claims, No Drawings

COMPOSITIONS CONTAINING ALKALI METAL SULFATE SALTS OF CONJUGATED ESTROGENS AND ANTIOXIDANTS AS STABILIZERS

RELATED APPLICATIONS

This Application is a continuation-in-part of Ser. No. 660,304, filed Feb. 23, 1976, now abandoned.

BACKGROUND OF THE INVENTION

1. Field of the Invention

This invention relates to the area of compositions containing synthetic conjugated estrogens and to the fields of compositions containing synthetic conjugated estrogens to be employed for replacement therapy of estrogen deficiency associated with menopausal syndrome, female hypogonadism (hypogenitalism), amenorrhea, female castration, or primary ovarian failure.

2. Description of the Prior Art

In U.S. Pat. No. 2,834,712, a process is described for preparing a mixture of conjugated estrogens from the urine of pregnant mares by absorption and extraction. The mixture consists primarily of water-soluble sulfates of a number of conjugated estrogens including estrone, 17α-estradiol, equilin, and equilenin. The mixture in the same proportion can also be duplicated essentially with synthetic estrogens. Whether synthetic or achieved from natural sources, mixtures of conjugated estrogens are applied by those skilled in the art therapeutically to relieve mental and bodily complaints occurring in the menopausal syndrome.

In relatively crude extracts containing conjugated estrogens from natural sources, natural but unknown stability constituents are apparently present, since it has been found that these products have a relatively high order of stability as compared to more highly purified estrogenic compositions, or those prepared from the synthetic conjugated estrogens. These natural conjugated estrogens are primarily derived from the urine of pregnant mares. Unfortunately, this extraction process makes the natural conjugated estrogens relatively expensive and, accordingly, they are available in limited quantities.

The pure synthetic estrogenic conjugates, while relatively inexpensive, have been found to be highly unstable, particularly in the presence of moisture. When moisture is present, even to a slight extent, as is the case with most tablets, an acid environment forms which quickly destroys the product. Obviously, the purified estrogenic conjugates are unstable when carried in aqueous media such as might be employed in injectable preparations. The instability of the estrogens is thought by those in the art to be due to hydrolysis which liberates hydrosulfuric acid and free estrogens which are for the most part inactive in the intended applications.

To combat the hydrolysis problem, it was proposed in U.S. Pat. No. 2,834,712 to add buffering agents which were capable of maintaining the pH of aqueous estrogen solutions at 6.5 to 7.5, with a preference for a slightly alkaline pH. While this approach might be satisfactory with conjugated estrogens derived from natural sources, it has been found that with synthetic estrogens, the presence of a buffer is only sufficient to provide stability for approximately six months when the estrogens are in dry tablet form. Unfortunately, it has been found that where the synthetic conjugates are present in an aqueous carrier buffered between pH 6.5 and 7.5, substantial hydrolysis has been found to occur almost immediately. A substantial need arose—the need for a synthetic conjugate which would not only be inexpensive but would retard hydrolysis and be stable for periods of time for beyond six months in order to give the corresponding pharmaceutical preparations acceptable shelf life.

The relevant prior art in the field of synthetic conjugated estrogens for use in treating menopausal syndrome, etc., was unfortunately thin. It is to be emphasized that several fields of art could be confused with the present fields at issue. In steroid chemistry, one field of art deals with the conjugated estrogens which are water-soluble, and another field deals in the chemistry of oil-soluble steroids. One field of art is concerned with conjugated estrogens used in curing vitamin deficiencies for patients with general inadequate or broadly restricted diets (for example, see *MODERN DRUG ENCYCLOPEDIA AND THERAPEUTIC INDEX*, (9th Edition, 1963) at 280–281; 517–521; 533; 1112–1114; 1376; 1389–1390; 1441), while another distant field of art is directed toward the use of conjugated estrogens for the replacement therapy (see Beall, U.S. Pat. No. 2,834,712) of estrogen deficiency associated with menopausal syndrome, female hypogonadism (hypogenitalism), amenorrhea, female castration, or primary ovarian failure. One art might employ salts as preservatives in non-conjugated estrogens (see *MODERN DRUG*, supra, at p. 1441, TRI-GENIK TM, whereas another art might employ the same as buffers for pH control. Chemists within a particular field of art (in this instance the field of synthetic and water-soluble conjugated estrogens for use in treating menopausal syndrome, etc.) do not pay the same attention to art outside their own field for good reason—generally the chemistry is so entirely different from field of art to field of art as to render the other teachings ineffectual.

While the following art will be discussed in some detail, most of it falls outside the purview of the present invention and is deemed by Applicant to be marginally, if at all, relevant. The art was presented in the related copending application, Ser. No. 660,304, filed Feb. 23, 1976. *MODERN DRUG ENCYCLOPEDIA AND THERAPEUTIC INDEX* (9th Edition, 1963) at 280–281 contains a reference to CLUVISOL GERIATRIC TM, which is a therapeutic combination of potent nutritional elements with steroids to meet the challenge of waning metabolic efficiency in old patients, with vitamin deficiencies, having a conjugated equine estrogens ("PREMARIN TM " by Ayerst Company) and a small fraction of Vitamin E in an amount falling outside the ranges prescribed by the present invention. The Vitamin E is present for purely therapeutic purposes, not as an antioxidant, as part of a "multi-vitamin". See also *PHYSICIAN'S DESK REFERENCE* at 584 (1977, by Medical Economics Co., C. E. Baker, Jr., Pub.).

Also, in *MODERN DRUG* at 517 is listed the prescription of ESTOPHEROL TABLETS TM (Pitman-Moore Company) having ethinyl estradiol and Vitamin E. However, ESTOPHEROL TABLETS TM do not contain a conjugated estrogen, and in fact ethinyl estradiol is stable without Vitamin E in numerous oral contraceptives. In the same art as ESTOPHEROL TM is ESTRADURIN TM (Ayerst Company), employing a non-conjugated estrogen (polyestradiol phosphate) and a small amount of nicotinamide as a stabilizing element (*MODERN DRUG* at 518). A number of companies market various ESTROGENIC SUBSTANCES (*MODERN DRUG* at 518–519), none of which mention the use of stabilizers.

*MODERN DRUG* at 553 lists FORMATRIX TM (Ayerst Company) containing in each tablet 1.25 mg of conjugated estrogens ("Premarin TM") and a very large amount of Vitamin C (not intended as an antioxidant) for the treatment of protein depletion and ascorbic acid deficiency (see *PHYSICIAN'S DESK REFERENCE*, supra, at 587).

"Premarin TM" of Ayerst Company is a preparation of orally-active, water-soluble and natural, conjugated estrogens derived from pregnant mares' urine, with no mention of any stabilizers being employed. *MODERN DRUG*, supra, at 1112–1114.

TESTROGYN TM, another preparation of Ascher Company, contains estradiol and testoserone (not conjugated estrogens), with sodium bisulfate as a preservative. *MODERN DRUG*, supra, 1376.

THEELIN TM (Parke-Davis Company) is a suspension of estrogenic steroids employing suitable preservatives. *MODERN DRUG*, supra, at 1389–1390. TRIGENIK TM (Savage Company) contains the non-conjugated estrogens estradiol, progesterone, and testosterone proprionate. A small amount of sodium meta-bisulfite is added as a preservative.

U.S. Pat. No. 2,324,348 (Anderson) teaches the use of ascorbic acid as an antioxidant in the unrelated arts of soaps and perfumes. No mention is made of employing Vitamin C in conjugated estrogens.

Louis C. Schroeter, "Sulfurous Acid Salts as Pharmaceutical Antioxidants" (50 *J. PHARMACEUTICAL SCIENCES* (No. 11) pp. 891 et seq. (1961) is a general article on the chemistry of the sulfurous acid salts as antioxidants. No mention is made of applying these salts to synthetic conjugated estrogens, and Schroeter never teaches any particularities of employing the salts, finding proper concentrations for applications controlling pH, etc. (See also Lachman, "Antioxidants and Chelating Agents as Stabilizers in Liquid Dosage Forms", D&CI at pp. 36–46 (1968).

Perhaps the most pertinent reference is British Pat. No. 806,779 to Schering, which discloses a concentrated aqueous solution of estrogens and certain acids (sodium estrone sulphate, sulphurous acid and glacial acetic acid or lactic acid) adjusted to a pH of 8.0 to 8.5, with buffers present to prevent discoloration of the estrone solution for use in cosmetic preparations.

Ludwig in U.S. Pat. No. 3,666,865 (1972) seeks to stabilize trans-diethylstilbestrol (trans - "DES"), a non-conjugated estrogen, with phenolic antioxidants such as 2,4,5-trihydroxybutyrophenone, urea, and sodium carbonate. No mention is made of an alkaline antioxidant formulation with the DES. U.S. Pat. No. 3,674,869 (1972) further claims to stabilize trans-DES with sulfur-containing compounds, e.g., thiophenol or ammonium sulfide.

Beall in U.S. Pat. No. 2,884,712 seeks to control pH between a range of 6.5 to 7.5 with certain buffering mixtures such as sodium or potassium dihydrogen phosphate and sodium or potassium hydroxide, etc. No mention is made of the use of any materials as antioxidants.

A. E. Smith in 41 C.A. 7484e (1974) and in "The Instability of Oestrogens In Solution", 5 *J. ENDOCRINOLOGY* pp. 152 et seq (1947) describes attempts to stabilize the non-conjugated estrogens dienestrol and stilbestrol with hydroquinone. Further listed are the estrone estradiol and hexestrol in sesame oil. See *MERCK INDEX* (9th Edition) at 547 (1968).

D. J. Nazir et al, 56 C.A. 2743i (1962) describes the use of α-tocopherol in vegetable oils as an antioxidant to decrease peroxide values. No mention is made of employing α-tocopherol in water-soluble estrogen. H. P. Kaufmann et al, in 58 C.A. 12785h–12786a (1963) describes the efficiency of sex hormones in retarding the oxidation of buffered K linoleate. The efficiency of the hormones are admitted to be less than α-tocopherol.

N. A. Zakhorova et al, in 65 C.A. 8981h–8982a (1966) investigated the antioxidant properties of certain naturally-occurring hormones. A. G. Stren-Kovskaya in 73 C.A. 1844t–1844a (1970) estimated the amounts of selected estrogens in animal fats and oils.

In U.S. Pat. No. 3,696,195 (1972) to Crivellaio et al, there are described pharmaceutical compositions which are stabilized with thioglycerol and thioglycolic acid.

Surprisingly then, it was found in the instant case that when the synthetic conjugated estrogens were mixed in proper proportions with selected antioxidants to form a novel composition with the pH maintained at a level of not less than about 7.0, that the composition obtained was stable and prevented oxidation and hydrolysis for extremely long periods (at least two years).

DESCRIPTION OF THE PREFERRED EMBODIMENTS

For the first time, it is now possible to initiate and maintain therapy for several female problems and diseases with synthetic conjugated estrogens, USP that have originated in the laboratory and not from equine wastes.

The present invention is a stabilized composition comprising an alkali metal sulfate salt of a steroid selected from the conjugated estrogens, i.e., the group consisting of estrone, equilin, 17α-dihydroequilin, equilenin, 17α-estradiol, 17β-dihydioequilin, 17β-dihydroequilenin, 17β-estradiol and mixtures thereof, and an antioxidant in a neutral or alkaline environment. Estrogen compositions stabilized according to the present invention are stable (i.e., less than about 5% hydrolysis) up to periods of at least about 24 months at room temperature. Preferable alkali metals are sodium and potassium.

Suitable antioxidants which can be employed include sodium and potassium sulfite, metabisulfite, bisulfites, thiosulfates, thioglycerol, thiosorbitol, cysteine hydrochloride and α-tocopherol (Vitamin E). Of course, as those skilled in the art will appreciate other antioxidants having different cations in complexes (ammonium, for example) instead of those in Groups IA and IIA of the Periodic Table can be used in achieving the objects of this invention. Preferable antioxidants are sodium and potassium sulfite, metabisulfite and α-tocopherol. While the pH of the composition should be at least about 7.0, it has been found that the likelihood of hydrolysis is further decreased by use of even more basic conditions. Therefore, it is preferred that the compositions exhibit a pH of at least above about 7.5. By the phrase "at least about 7.0" we mean all pH levels from slightly below 7.0 up to 14.0.

Effective amounts of alkaline antioxidants vary with the type of administration. To provide stable estrogen compositions (i.e., tablets, parenterals, etc.), generally from 0.25 to 6 moles of antioxidant are present for each mole of alkali metal synthetic estrogen sulfate, although smaller amounts may be effective for specific combinations. For parenteral preparations containing from 5 to 25 mg of alkali metal synthetic estrogen sulfate (i.e., estrogen conjugates) from 1 to 6 moles of antioxidant are employed per mole of the synthetic estrogen conjugates. For oral tablets, from about 1 to 5 moles of antioxidant per mole of estrogen conjugates are employed. The synthetic conjugated estrogens can also be employed in the form of gelatin capsules wherein from 0.25 to 2 moles of antioxidant are present for each mole of synthetic estrogen conjugates. Generally, oral dosage forms such as tablets or gelatin capsules contain from 0.2 to about 20 mg of estrogen conjugates in each dose (e.g., tablet or capsule). Most preferably, a combination of sodium estrone sulfate, sodium equilin sulfate, and 17α-dihydroequilin sodium sulfate is employed in a weight ratio of about 6:3:1, wherein the total conjugated estrogen content per dose is administered in a tablet or gelatin form of a multiple of about 0.625 mg. These weight tablets are marketed under the name "GENESIS" by Organon Inc., of West Orange, N.J.

In addition to the conjugated estrogens and antioxidants, the compositions of the invention also include other amounts of compounds commonly employed in pharmaceutical compositions and known to those skilled in the art, such as: inert fillers (e.g., lactose, calcium phosphate, microcrystalline cellulose), dyes and colorants, disintegrating agents (hydrated silica), binding agents (e.g., methyl cellulose, amylopectin), anticaking agents (e.g., Silicon Dioxide), lubricants (e.g., stearic acid, magnesium stearates), and suspending agents (vegetable oil).

The stabilized estrogenic compositions of the invention can be prepared either in solution or dry form. Solutions of conjugated estrogens are useful in injectable compositions in the treatment of abnormal functional uterine bleeding. The dose required to produce hemostasis is relatively large and may range from 2.5 mg to 12.5 mg of conjugated estrogen in the novel composition or more daily given in divided doses. Bleeding will usually stop in 2 to 5 days assuming adequate dosage. The effective dose should be continued for the next twenty (20) days with concomitant progestin therapy during the last five (5) days in order to recycle the patient. If subsequent treatment cycles are required, one may treat the patient as for amenorrhea below.

For female hypogonadism (hypogenitalism), the dosage requirements and duration of therapy required to prime a potentially responsive endometrium will vary depending on the degree of estrogen deficiency. Cyclic therapy is recommended using doses of 2.5 to 7.5 mg in divided daily doses for twenty (20) days of a thirty-day cycle. If bleeding does not occur by the end of the ten-day rest period, then cyclic and sequential therapy with the novel compositions of my invention and a suitable progestin, given on the fifth day after bleeding has started, should be instituted and continued.

For amenorrhea, dosage recommendations are the same as above except that the progestin is given concomitantly from the sixteenth to the twentieth day of each cycle to mimic the natural pattern. In the event that breakthrough bleeding occurs, therapy should be discontinued at the point and resumed again on the fifth day of bleeding.

It is to be noted that for parenteral preparations, an especially desirable range of antioxidant is between 20 and 40% by weight of the total conjugated estrogens. In preparing the injectable product, the conjugated estrogens are combined with the antioxidant and other commonly employed materials, all dissolved in an aqueous vehicle. The pH of the solution is carefully adjusted to from about 7.0 to about 8.0, taking care that the pH does not fall below about 6.9. The solution is filtered through a bacteriological membrane filter and filled in vials or ampoules and freeze-dried. Such solutions can have any pH above the range of 7.0 or 8.0 set forth above, as only at the lower end of the pH range, e.g., pH 7.0, has been found to be critical for stability. The freeze-dried preparations have been found to be stable for periods as long as twenty-four (24) months and even longer. They are reconstituted prior to use with an isotonic saline solution.

In its most important application and in addition to the utilities noted above, the stabilized synthetic conjugates may be employed orally in the form of tablets for the treatment of menopausal syndrome. Generally, the tablets will contain from about 0.3 to about 2.5 mg. of total conjugated estrogens, although much higher amounts can be employed. (The dose required to bring symptoms under control is relatively large and may even range from 1.25 mg. to 3.75 mg or even more daily in divided doses). When this has been accomplished, dosage should then be established. This will usually be 0.625 mg or 1.25 mg or even less.

GENESIS TM may also be indicated for female castration, primary ovarian failure, senile vaginitis and kraurosis vulvae (0.3 to 1.25 mg daily adequate in most patients), for palliation of inoperable breast cancer in women with progressing or roentgen resistant disease who are more than five (5) years post-menopausal (10 mg thrice daily is operable), and palliation of prostatic cancer (1.25 to 2.5 mg thrice daily) when castration is not feasible or when castration failures or delayed escope following a response to castration have not occurred.

A very convenient method of preparing the tablets is to prepare aqueous solutions from the conjugated estrogens and the antioxidant. The resulting solutions are used to granulate the various powdered components of the formulation. The granules are dried, lubricated and compacted into tablet form which may receive any of the customary coatings such as sugar or film coating. Coatings are generally applied to protect the active ingredients. However, and unexpectedly, it has been found that even in the absence of a coating, the tablet form is stable for extended periods (e.g., 24 months or longer) and, therefore, a coating need not be employed.

For the preparation of a soft gelatin capsule, the water-soluble conjugated estrogen-containing compositions are dispersed in a vegetable oil, e.g., for example, soybean oil. A liquid and suitable organic antioxidant, preferably dl-α-tocopherol is used as an antioxidant and microfine precipitated silica is added as dispersing agent. The oil suspension is sealed in a soft gelatin capsule of the desired size and shape.

The mechanism by which the antioxidants function to stabilize the conjugated estrogens is not completely understood. However, it is well-known that acid conditions tend to cause hydrolysis of the conjugates. In this regard, U.S. Pat. No. 2,834,712 teaches that buffering agents should be employed to maintain pH levels between 6.5 and 7.5. However, it must be stated even in the presence of appropriate buffers, if the suitable antioxidants are not present, the estrogen conjugates are stable only for periods up to approximately six months. Use of antioxidants in addition at a pH of not less than 7 provides stabilization both to solutions and "dry" preparations for up to at least about 24 months, which is the limit of testing so far conducted. It is hypothesized here that the primary cause of instability is not acid hydrolysis but rather oxidation of components in the estrogen preparation. Oxidation may create acidic conditions which cause hydrolysis. Hydrolysis is, therefore, minimized by minimizing oxidation.

The above-described invention is more particularly set forth in the following Examples which are to be construed for purposes of illustration only and not for limitation of my invention. Obvious modifications from the following Examples can be made to accommodate various synthetic conjugated estrogens and antioxidants in various administrations.

EXAMPLE I

Preparation of a batch of 1,000,000 tablets of 2.5 mg of synthetic conjugated estrogens per tablet.

The following conventional ingredients are admixed and blended, screened, dried, and reduced to a fine microgranulation.

| | |
|---|---|
| Lactose (anhydrous) | 97.117 kg. |
| Microcrystalline cellulose (Avicel ® by the FMC Corp. of Marcushook, Pa., 19061) | 62.00 kg. |
| Corn Starch | 24.80 kg. |
| Methyl cellulose (Methocel 60 HG, 50 cps) | 3.75 kg. |
| Amylopectin | 3.75 kg. |

A blend containing 2.750 kg. of selected synthetic conjugated estrogens[1], 1.833 kg. of "Tris"[2], and 1.50 kg of anhydrous sodium sulfite is added to a microgranulation of the above ingredients. Magnesium stearate (1.0 kg.) and 1.5 kg. of Silicon Dioxide (Syloid 244) are added as lubricants. The resulting blend is compressed into tablets of 200 mg.

[1]—The synthetic conjugated estrogens here are a mixture consisting of (on a weight basis) 10% 17α-dihydroequilin sodium sulfate, 30% equilin sodium sulfate and 60% estrone sodium sulfate, the same as in "GENESIS ®".
[2]—"Tris" is 2-amino-2-hydroxymethyl-1.3-propanediol.

The estrogen conjugates are prepared synthetically and the "Tris" functions as an initial stabilizer temporarily until the sodium sulfite of the invention is added.

EXAMPLE III

Conjugated Estrogens + Non-antioxidant Buffer

Examples III through V were conducted by using aqueous solutions of conjugated estrogens of the following composition:

| | |
|---|---|
| Sodium 17α-dihydroequilin sulfate | 18 mg. |
| Sodium equilin sulfate | 54 mg. |
| Sodium estrone sulfate | 108 mg. |
| Tris | 120 mg. |
| Water | 30 ml. |

The aqueous conjugated solution was buffered to pH 7.0 using a phosphate buffer of pH 7.0. To a second aqueous solution, 300 mg. of sodium sulfite was added and the solution maintained at pH of 7.0. After storage for two weeks at 37° C., the buffered solution exhibited a red color indicating the presence of oxidized equilin and 17α-dihydroequilin. The sodium sulfite solution remained colorless (no oxidation) and clear (no hydrolysis). Analysis by gas chromatography indicated that no free steroids were present. By contrast, analysis of the first buffered solution without antioxidants showed that a precipitate of free steroids was present indicating that in the two-week period approximately 50% of the estrogen conjugates had decomposed. This Example indicates that for a given short period of time (less than the full two-year period mentioned above), the solution with the suitable antioxidants was significantly more stable than prior art compositions.

EXAMPLE IV

Stability at pH 7.0-7.5

An aqueous solution (30 ml.) of conjugated estrogens as in Example III was neutralized to a pH of about 7.0 to about 7.5 with one normal sulfuric acid. 300 mg. of sodium sulfite was added which brought the pH to about 9.7. Using one normal $H_2SO_4$, the pH was then adjusted to 7.0. Similar solutions were prepared at pH

| | Percentages of Constiuents in 2.50 mg of Active Synthetic Conjugated Estrogens | | | |
|---|---|---|---|---|
| Time Period | ±10% of Sodium 17α-Dihydroequilin Sulfate | ±30% of Sodium Equilin Sulfate | ±60% of Sodium Estrone Sulfate | 90-110% of Total Conjugated Estrogen 2.50 mg/tablet (Excess of conjugated estrogen above 2.5 mg per tablet) |
| Initial | 8.9% | 29.3% | 61.8% | 109% |
| 6 weeks-45° C. | 9.8% | 29.9% | 60.3% | 107% |
| 13 weeks-37° C. | 7.7% | 30.5% | 61.8% | 99% |
| 6 months-Rm. Temp. (22° C.) | 9.8% | 29.1% | 61.1% | 105% |
| 12 months-Rm. Temp. (22° C.) | 9.9% | 29.7% | 60.4% | 108% |
| 24 months-Rm. Temp. (22° C.) | 8.6% | 28.7% | 62.7% | 104% |

The percentages represent the percentum weight of the active (or estrogen) ingredients in the approximated 2.5 mg. of the entire composition.

increments of 0.2, i.e., 7.2, 7.4, and 7.6. After storage for five days at 60° C., all solutions remained clear and only a trace of free steroids could be detected using thin layer chromatography to analyze a chloroform extract of the aqueous solution.

Repeating the above procedures, conjugate solutions were found to be stable at pH 6.5–7.0. Only at pH of less than about 4.5 did substantial hydrolysis occur. For example, at pH 3.16, about 20% of the conjugated estrogens had been hydrolyzed after the five-day storage period. This Example indicates that even at abusive low pH ranges not within the scope of our invention, the novel composition of our invention have surprisingly good stability, although for practical applications the pH should be maintained at a pH of more than about 7.0.

EXAMPLE V

To determine the effect of Tris" alone, solutions were prepared as in Example IV at a pH of about 7.0 with the difference that one solution contained sodium sulfite whereas in the second solution only Tris was used as the stabilizer. Both solutions were stored for two weeks at 37° C. The second solution (without sodium sulfite) had a slight precipitate and a chloroform extract indicated the presence of free steroids when analyzed by TLC. The first solution (with sodium sulfite) was clear and chloroform extraction was negative as to free steroids. This Example indicates that ordinary constituents such as "Tris" added which control pH only within the ranges of this invention will not operate to extend shelf life in the absence of an effective amount of a suitable antioxidant.

The above Examples were illustrative only, were not intended to limit the scope of the invention, but to give some guidance to those skilled in the art in the preparation of the desired novel compositions containing synthesized conjugated estrogen sulfate salts and effective amounts of one or more suitable antioxidants.

While the novel compositions represent a benefit for those women afflicted with certain conditions, use of the novel compositions of my invention, like all estrogen-containing pharmaceuticals, is not without some unknown risks as will be appreciated by those skilled in the art.

An increased risk of thromboembolic disease associated with the use of oral contraceptives containing estrogens and progestins has now been conclusively established. Retrospective studies have shown a statistically significant association between thrombophlebitis, pulmonary embolism, and cerebral thrombosis and embolism and the use of these drugs. There have been three principal studies in Great Britain and one in the United States leading to this conclusion:
1. Royal College of General Practitioners: Oral Contraception and Thrombo-Embolic Disease. J. Coll. Gen. Pract. 13:267–279, 1967.
2. Inman, W. H. W. and Vessey, M. P., Investigation of Deaths from Pulmonary, Coronary and Cerebral Thrombosis and Embolism in Women in Child-Bearing Age, Brit. Med. J. 2:193–199, 1968.
3. Vessey, M. P. and Doll, R., Investigation of Relation Between Use of Oral Contraceptives and Thromboembolic Disease. A Further Report. Brit. Med. J., 2:651–657, 1969, and
4. Sartwell, P. E., Masi, A. T., Arthes, F. G., Green, G. R., and Smith, H. E., Thromboembolism and Oral Contraceptives: An Epidemiological Case-Control Study. Am. J..Epidem. 90:365–380, (November) 1969.

As a result of these studies, it has been estimated that users of oral contraceptives containing estrogens are 4 to 7 times more likely than non-users to develop thromboembolic disease without evident cause. The American study also indicated that the increased risk did not persist after discontinuation, nor was it enhanced by long continued administration. Although the American study was not designed to evaluate a difference between products, it did suggest that there might be an increased risk of thromboembolic disease in users of sequential products. Confirmation of this finding requires further study.

In a more recent analysis of data derived from several national adverse reaction reporting systems, British investigators concluded that the risk of thromboembolism, including coronary thrombosis, is directly related to the dose of estrogen used in oral contraceptive products. (See Inman, W. H. W., Vessey, M. P., Westerholm, B., Engelund, A., Thromboembolic Disease and the Steroidal Content of Oral Contraceptives, Brit. Med. J., 25th April, 1970.)

Their analysis did suggest, however, that the quantity of estrogen may not be the sole factor involved. Nevertheless, in view of this study, as well as others that have demonstrated a positive relationship between estrogens and thromboembolism, it would seem prudent and in keeping with basic therapeutic principles, to utilize, whenever feasible, the smallest effective dose of estrogen in treating patients.

Risks associated with certain other known adverse reactions, such as elevated blood pressure, liver dysfunction, and reduced tolerance to carbohydrate, have not as yet been quantitated.

Long term administration of both natural and synthetic estrogens in subprimate animal species in multiples of the human dose increases the frequency for some animal carcinomas. These data cannot be transposed directly to man. The possible carcinogenicity due to the estrogens can neither be confirmed nor refuted at this time. Close clinical surveillance of all women taking estrogens must be continued.

It has been reported in a recent study done in the United States that the maternal ingestion of diethylstilbestrol during pregnancy appears to increase the risk of vaginal adenocarcinoma developing years later in the offspring exposed: Herbst et al—Adenocarcinoma of the Vagina—New England Journal of Medicine, Vol. 284, Number 16 (April 22, 1971).

Of course, it must be emphasized that no toxic side effects have so far been found with the novel compositions of matter of this invention. Of course, in the administration of the novel compositions of our invention should certain manifestations occur of the following type, medication should be withdrawn.

Estrogens may be excreted in the mother's milk and an estrogenic effect upon the infant has been described. The long range effect on the nursing infant cannot be determined at this time.

Hypercalcemia may occur in as many as 15% of breast cancer patients with metastases and this usually indicates progression of bone metastases. This occurrence depends neither on dose nor on immobilization. In the presence of untoward effects such as progression of the cancer or hypercalcemia, the effect of estrogen medication should be stopped.

Enteric coating retards absorption from the gastrointestinal tract and this form of therapy should not be used when rapid action is desired.

A statistically significant association has been reported between maternal ingestion during pregnancy of diethylstelbestrol and the occurrence of vaginal carcinoma developing years later in the offspring. Whether such an association is applicable to all estrogens is not known at this time. In any event, estrogens are not indicated for use during pregnancy.

It must be noted that a statistically significant association has been demonstrated between use of estrogen-progestin oral contraceptives and the following serious reactions: thrombophlebitis, cerebral thrombosis, pulmonary embolism.

Although available evidence is suggestive of an association, such a relationship has been neither confirmed nor refuted for the following serious reactions: coronary thrombosis, neuro-ocular lesions (e.g. retinal thrombosis and optic neuritis).

The following adverse reactions are known to occur in patients receiving estrogens: nausea, vomiting, anorexia, gastrointestinal symptoms (such as abdominal cramps or bloating), edema, breakthrough bleeding, spotting or withdrawal bleeding, breast tenderness and enlargement, change in body weight (increase or decrease), headache, increased cervical mucus, allergic rash, loss of libido and gynecomastia in the male, reactivation of endometriosis, aggravation of migraine headaches, hepatic cutaneous porphyria becoming manifest, cholestatic jaundice, rise in blood pressure in susceptible individuals, mental depression, cystitis-like syndrome, loss of scalp hair, erythema nodosum, hemorrhagic eruption, premenstrual-like syndrome, changes in libido, changes in appetite, nervousness, dizziness, fatigue, backache, erythema multiforme, itching, possible diminution in lactation when given immediately post-partum, irritability, malaise.

Therefore, although no relationship has been shown to exist between the compositions of my invention and the above adverse reactions, the following precautions should be observed by those administering the compositions of my invention:

1. Because normal endogenous hormone production varies individually, certain patients may be unusually responsive to estrogenic therapy and may respond with undesirable manifestation of excessive estrogenic stimulation, such as abnormal or excessive uterine bleeding, mastodynia, edema, etc.

2. Because of estrogen induced salt and water retention, these drugs should be used with caution in patients with epilepsy, migraine, asthma, cardiac or renal disease.

3. Patients with a history of psychic depression should be carefully observed and the drug discontinued if the depression recurs to a serious degree.

4. In the event that any unexplained or excessive vaginal bleeding would occur while on estrogen therapy, nonfunctional causes should be borne in mind. The drug should be discontinued and a thorough investigation made as to the cause, being certain to rule out the possibility of malignancy.

5. Pre-existing uterine fibromyomata may increase in size while using this product, therefore, patients should be examined at regular intervals while receiving estrogenic therapy.

6. Women with a strong family history of cancer, recurrent chronic cystic mastitis, or abnormal mammograms should be administered estrogens with caution.

7. Because of a possible decrease in glucose tolerance, diabetic patients should be followed closely.

8. Because estrogens influence the metabolism of calcium and phosphorus, they should be used with caution in patients with certain metabolic bone diseases that are associated with hypercalcemia or in patients with renal insufficiency.

9. The pathologist should be advised of estrogen therapy when relevant specimens are submitted.

10. Because of the effects of estrogens on epiphyseal closure, they should be used judiciously in young patients in whom bone growth is not complete.

11. A pre-treatment physical examination should include special reference to breast and pelvic organs as well as a Papanicolaou smear since estrogens have been known to produce tumors, some of them malignant, in five species of animals.

12. When large doses of estrogens are used, urinary stress incontinence may occur in nonpregnant females.

13. Prolonged high doses of estrogens will inhibit anterior pituitary functions. This should be borne in mind when treating patients in whom fertility is desired.

14. Continuous use of estrogens will result in prolonged stimulation of the endometrium and breast. In order to avoid this, oral estrogens should be administered cyclically in the menopausal or hypogonadal patient.

15. The age of the patient constitutes no absolute limiting factor, although treatment with estrogens may mask the onset of the climacteric.

16. Certain endocrine and liver function tests may be affected by treatment with estrogens. If such tests are abnormal in a patient taking these drugs it is recommended that they be repeated after the drug has been withdrawn for two months.

17. Any possible influence of prolonged estrogen therapy on pituitary, ovarian, adrenal, hepatic, or uterine function awaits further study.

The following claims represent the bounds of my Invention, with variances obvious to those skilled in the art able to be substituted without departing from the scope of the Invention.

I claim as my invention:

1. A stabilized therapeutic preparation exhibiting no oxidation and less than about 5% hydrolysis up to at least 24 months, said preparation adapted for treatment of menopausal syndrome, female hypogonadism, amenorrhea, female castration, primary ovarian failure, abnormal uterine bleeding due to hormonal imbalance, and senile vaginitis, consisting essentially of:
   at least one alkali metal sulfate salt of a synthetic conjugated estrogen selected from the group consisting of estrone, equilin, 17α-dihydroequilin, 17β-hydroequilin, 17β-estradiol, 17α-estradiol, equilenin, and 17β-dihydroequilenin in estrogenically effective proportions, and
   an antioxidant effective amount of at least one suitable antioxidant for said alkali metal sulfate salt of said synthetic conjugated estrogen selected from the group consisting of sodium sulfite, potassium sulfite, sodium metabisulfite, potassium metabisulfite, sodium bisulfite, potassium bisulfite, sodium thiosulfate, potassium thiosulfate, thioglycerol, thiosorbitol, cysteine hydrochloride, and α-tocopherol, wherein the preparation is maintained at an alkalinity corresponding to a pH of not less than about 7.0.

2. The preparation of claim 1 in unit dosage form to treat abnormal uterine bleeding or discomfort in menopausal syndrome containing between about 5 and about 25 mg. of synthetic conjugated estrogen.

3. The pharmaceutical composition of claim 1, wherein said antioxidant is present in an amount of from about 2.5 to about 6 moles of antioxidant per mole of alkali metal salt of synthetic conjugated estrogens.

4. The preparation of claim 1 wherein the alkali metal is selected from sodium and potassium.

5. The preparation of claim 4, wherein the antioxidants are selected from the group consisting of sodium sulfite, potassium sulfite, and dl$\alpha$-tocopherol.

6. The preparation of claim 4, wherein the pH is maintained at an alkalinity of about 7.0 to about 8.5.

7. The preparation of claim 4, wherein the conjugated estrogens comprise a mixture of sodium estrone sulfate, sodium equilin sulfate, and 17$\alpha$-dihydroequilin sodium sulfate which are present in a weight ratio to each other of about 6:3:1, respectively.

8. The preparation of claim 4 in unit dosage adapted for oral administration to treat discomfort in menopausal syndrome, containing about 0.2 to about 20 mg. of synthetic conjugated estrogens.

9. The preparation of claim 8, wherein the synthetic conjugated estrogens are present from about 0.3 to about 2.5 mg. per dose.

10. A method for stabilizing therapeutic compositions that are adapted for treatment of menopausal syndrome, female hypogonadism, amenorrhea, female castration, primary ovarian failure, abnormal uterine bleeding due to hormonal imbalance, and senile vaginitis, and exhibiting no oxidation and less than about 5% hydrolysis for times greater up to at least 24 months, which compositions consist essentially of at least one alkali metal sulfate salt of a synthetic conjugated estrogen selected from the group consisting of estrone, equilin, 17$\alpha$-dihydroequilin, 17$\beta$-hydroequilin, 17$\beta$-estradiol, 17$\alpha$-estradiol, equilinen, and 17$\beta$-dihydroequilenin in estrogenically effective proportions, said method comprising:

adding an antioxidant effective amount of at least one suitable antioxidant for said alkali metal sulfate salt of said synthetic confugated estrogen selected from the group consisting of sodium sulfite, potassium sulfite, sodium metabisulfite, potassium metabisulfite, sodium bisulfite, potassium bisulfite, sodium thiosulfate, potassium thiosulfate, thioglycerol, thiosorbitol, cysteine hydrochloride, and $\alpha$-tocopherol, wherein the preparation is maintained at an alkalinity corresponding to a pH of not less than about 7.0.

* * * * *